United States Patent
Hatley, Jr.

(10) Patent No.: US 6,305,934 B1
(45) Date of Patent: Oct. 23, 2001

(54) MULTIFUNCTION SYRINGE FOR REPAIRING TEETH

(76) Inventor: Bill H. Hatley, Jr., 319 N. Second St., Albemarle, NC (US) 28001

(*) Notice: Subject to any disclaimer, the term of this patent is extended or adjusted under 35 U.S.C. 154(b) by 0 days.

(21) Appl. No.: 09/686,290

(22) Filed: Oct. 11, 2000

(51) Int. Cl.⁷ .................................................. A61C 17/00
(52) U.S. Cl. ................................................ 433/80; 433/88
(58) Field of Search .................................. 433/80, 81, 82, 433/83, 88, 89

(56) References Cited

U.S. PATENT DOCUMENTS

| | | |
|---|---|---|
| 2,812,765 | 11/1957 | Tofflemire . |
| 3,593,423 | 7/1971 | Jones et al. . |
| 3,718,973 | 3/1973 | Slater et al. . |
| 3,745,655 | 7/1973 | Malmin . |
| 3,807,048 | 4/1974 | Malmin . |
| 3,816,921 | 6/1974 | Malmin . |
| 4,217,101 * | 8/1980 | Loge ...................................... 433/126 |
| 4,472,141 | 9/1984 | Dragan . |
| 4,648,840 | 3/1987 | Conger, Sr. . |
| 4,673,353 | 6/1987 | Nevin . |
| 4,768,955 | 9/1988 | Hirdes . |
| 4,820,152 | 4/1989 | Warrin et al. . |
| 4,826,431 | 5/1989 | Fujimura et al. . |
| 4,886,452 * | 12/1989 | Löhn ...................................... 433/80 |
| 4,902,225 | 2/1990 | Lohn . |
| 4,968,249 * | 11/1990 | Löhn ...................................... 433/80 |
| 5,199,604 * | 4/1993 | Palmer ................................... 433/80 |
| 5,334,016 | 8/1994 | Goldsmith et al. . |
| 5,415,543 | 5/1995 | Rozmajzl, Jr. . |
| 5,456,672 * | 10/1995 | Diederich et al. ...................... 433/80 |
| 5,658,144 * | 8/1997 | Tinder et al. .......................... 433/88 |
| 5,848,893 * | 12/1998 | Martin et al. .......................... 433/80 |
| 5,899,692 * | 5/1999 | Davis et al. ........................... 433/80 |
| 5,927,975 * | 7/1999 | Esrock .................................. 433/80 |
| 6,183,252 * | 2/2001 | Huang .................................. 433/80 |
| 6,217,328 * | 4/2001 | Oliver ................................... 433/80 |
| 6,238,211 * | 5/2001 | Esrock .................................. 433/80 |
| 6,247,929 * | 6/2001 | Bachman et al. ...................... 433/80 |

\* cited by examiner

Primary Examiner—Ralph A. Lewis
(74) Attorney, Agent, or Firm—Summa & Allan, P.A.

(57) ABSTRACT

A multifunction hand-held syringe for use in dental restorative procedures in conjunction with conventional instrument delivery systems. The multi-function syringe includes multiple reservoirs for containing viscous material (e.g., resin and etchant), conduits for delivering etchant, water, air, and resin to an affected area, wherein the syringe is capable of delivering etchant, water, air, and resin to an affected area on the tooth surface. The multi-function hand-held syringe is further characterized by a light emitting source capable of curing the resin extruded onto the affected area. The syringe also includes a detachable shank such that the nozzle may be removed for cleaning. The syringe also includes a coupling for connecting the syringe to conventional instrument delivery systems such that the syringe is portable.

93 Claims, 2 Drawing Sheets

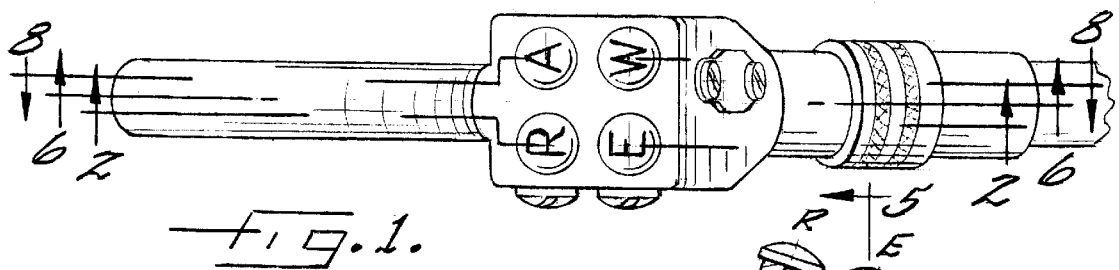
Fig.1.
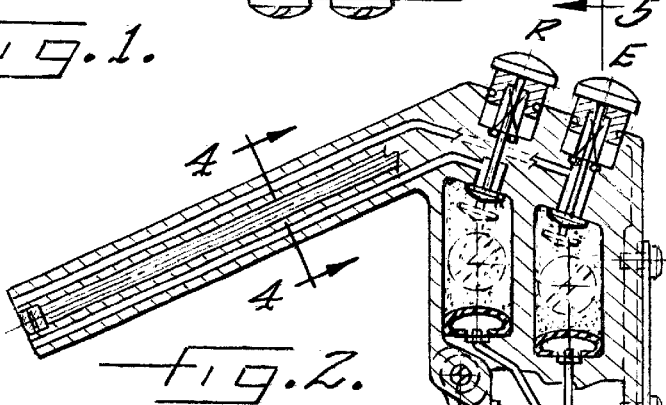
Fig.2.
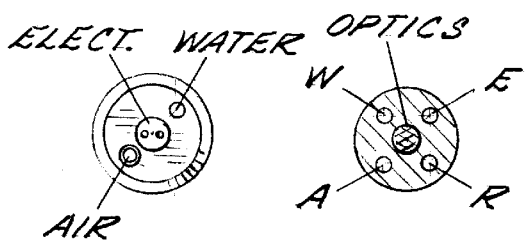
Fig.3.  Fig.4.
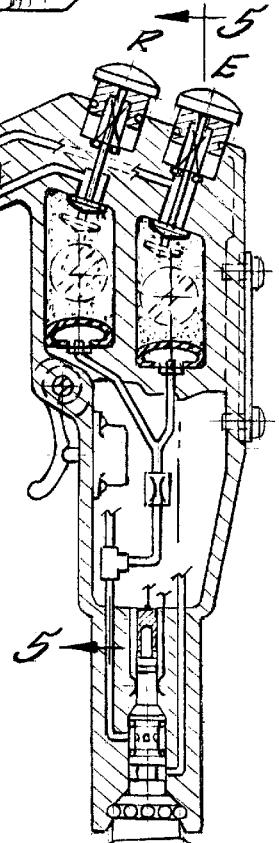
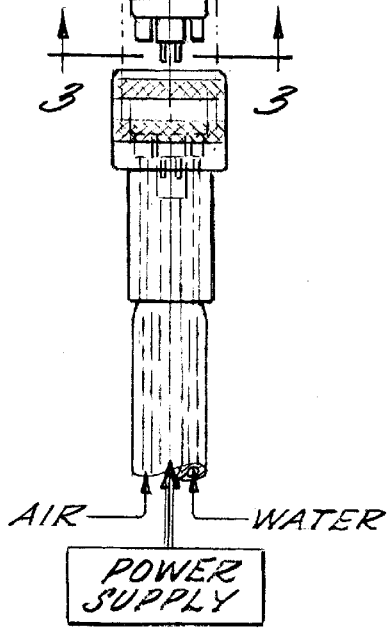
Fig.5.

MULTIFUNCTION SYRINGE FOR REPAIRING TEETH

FIELD OF THE INVENTION

The invention relates to an apparatus for use in repairing teeth. In particular, the invention relates to a hand-held multifunction syringe for repairing teeth having multiple reservoirs for containing viscous material (e.g., resin and etchant), conduits for delivering etchant, water, air, and resin to an affected area, wherein the syringe is capable of delivering etchant, water, air, and resin to the affected area, and further characterized by a light emitting source capable of curing the resin extruded onto the affected area.

BACKGROUND OF THE INVENTION

The principles of adhesion, wherein the molecules of one substance bind or are attracted to molecules of another substance necessarily play a significant role in dentistry. For example, the adhesion process directly affects the dental restoration of teeth. In brief, adhesion is a surface attachment process wherein the attachment of one substance (e.g., resin or resin composite material) to another (e.g., enamel or dentin on a tooth structure) can be accomplished by mechanical bonding. As applied to dentistry, mechanical bonding involves the penetration of an adhesive or resin into crevices on the surface of the tooth structure.

Current examples of mechanical bonding used in dentistry includes the use of resin restorative materials. Nevertheless, these resins are not capable of truly adhering to a tooth structure. In a method known to those skilled in the art, a fluid or semi-viscous resin is used to create a mechanical bond between the resin and the tooth structure because the flowing resin readily penetrates into the surface defects (i.e., crevices) of the tooth structure. Subsequently, once the fluid resin hardens, the plurality of resin projections embedded in the tooth surface provides a base for mechanical attachment. The procedure for using a fluid or semi-viscous liquid (e.g., resin or adhesive) is referred to as wetting. If the fluid does not wet the entire surface of the affected area of the tooth, adhesion between, for example, resin and the tooth structure will be negligible or non-existent. Poor adhesion or non-adhesion between the tooth structure and a restorative material often results in leakage adjacent to the restored area. This leakage typically leads to staining, secondary tooth decay, and irritation to the pulp of the tooth structure. As discussed below, a number of factors such as the cleanliness of the surface influence the ability of an adhesive or resin to wet the surface of the tooth surface.

A popular technique for applying resin restorative materials includes treating the enamel of the tooth structure with phosphoric acid prior to applying the resin. This technique is commonly referred to as the acid-etching technique. The acid creates microscopic pores in the enamel surface of the tooth structure into which the resin subsequently flows when delivered into the etched area. As referenced above, the resin projections jutting into the pores in the enamel surface of the tooth enhance the mechanical retention of the restoration upon hardening, thereby reducing the possibility of interfacial marginal leakage.

The most significant problem associated with bonding resins to the tooth structure during restorative procedures is contamination by water or a patient's saliva. During routine dental restorative procedures, a dentist must constantly attempt to keep the affected area of a tooth dry. Although tools such as dental dams, air jets, and suction devices are used to prevent saliva from encroaching upon the affected area, some saliva inevitably reaches portions of the affected area during the restorative procedure. This situation is especially true during dental restorations whereby the dentist must restore the tooth in a stepwise fashion involving multiple dental instruments. During a routine repair of a decayed area on the tooth surface, the dentist must first retrieve an acid application tool (e.g., syringe) from a storage rack, etch the decayed area for approximately fifteen seconds, and then replace the acid applicator on the storage rack. Upon etching the tooth, the dentist retrieves an air and water syringe from the storage rack, and rinses the acid etchant off the enamel with a stream of water for approximately ten to twenty seconds. Next, the dentist applies air to the affected area in order to dry the same while attempting to exclude all moisture. Upon returning the air and water syringe to the rack, the dentist must quickly retrieve a resin applicator from the storage rack and apply resins to the prepared area before the patient's saliva reaches the prepared area. The etched surface must be kept clean and dry until the dentist applies the resin in order to form a sufficient bond. Upon returning the resin applicator to the storage rack, the dentist retrieves a light source and exposes the affected area in order to cure the resin. Inevitably, some moisture will reach the affected area during the lengthy process described above as a result of the patient moving his tongue over the affected area, attempting to swallow, or partially closing the mouth.

Adding to the difficulty of keeping the prepared area dry is the fact that the inorganic bonds of the tooth structure have a strong affinity for water. As result, the presence of at least a small layer of water on the surface of the prepared cavity must be accepted. This water layer reduces the surface energy and thus may reduce the wetting of the restorative material.

As referenced above, the most effective procedure for enhancing mechanical bonding commonly used by dentists is the acid-etch technique. The acid-etch technique has promoted the use of resin-based restorative materials because it provides a strong mechanical bond between resin and enamel/dentin (e.g., resin bonded metal retainers, porcelain inlaid veneers, and orthodontic braces). Accordingly, dentists typically use thermoplastic resins to restore and replace missing teeth. Most resin systems used in dentistry are based on methacrylates, and methyl methacrylate in particular.

Specifically, the process for bonding enamel and resin-based restorative materials involves the etching of the enamel to promote selective disintegration of the tooth enamel resulting in a microporous surface. Etched enamel (as opposed to normal enamel) is characterized by a high surface energy, and allows a resin to readily wet the surface and penetrate into the microporosity. Upon penetrating the microporosity of the etched enamel the resin can be polymerized to form a mechanical bond to the enamel. Polymerization occurs through a series of chemical reactions by which a macromolecule (i.e., polymer) is formed from large numbers of molecules known as monomers. Polymerization can occur either by series of localized reactions, commonly referred to as step growth polymerization, or by simple addition reactions, commonly referred to as addition polymerization. Most dental resins are polymerized by addition polymerization.

The resin projections (commonly referred to as "tags") may penetrate ten to twenty microns ($\mu$) into the pores of the enamel, but their links are dependent on the enamel etching time. The standard acid used to produce the porous enamel is phosphoric acid at concentrations between thirty to fifty percent. Typically, dentists prefer an etchant in a gel form because the gel provides control over the exact placement of the etchant on the affected area. The application time of the etchant may vary depending on the degree of decay of the tooth. For example, a tooth having a high fluoride content resulting from fluoride treatment (i.e., treated water supply) may require a longer etching time as compared to a non-treated tooth. A common procedure includes applying the etchant for fifteen seconds.

Accordingly, upon etching the tooth, the dentist rinses the acid etchant off the enamel with a stream of water for approximately twenty seconds, then directs a jet of air across the affected area until the enamel and dentin is sufficiently dry. As discussed above, in order to form a sufficient bond the etched surface must be kept clean and dry until the dentist applies the resin. Because enamel etching raises the surface energy of the enamel, contamination can readily occur because of the tendency to reduce the energy level of the etched surface. A potential reduction in surface energy makes it more difficult to wet the surface with a bonding resin that may have a higher surface energy than that of the contaminated surface. Thus minimal contact with saliva or blood can prevent effective resin tag formation and severely reduce the bond strength.

Commonly used resins include acrylic resins, methyl methacrylate, poly methyl methacrylate, and multifunctional methacrylate and acrylate resins. Plasticizers are often added to resins to reduce the softening or fusion temperatures. Synthetic resins are popular restorative materials because they are insoluble, aesthetic, insensitive to dehydration, inexpensive, and relatively easy to manipulate. Modern composite materials are comprised of a resin matrix, inorganic filler particles, and additional components to enhance the effectiveness and durability of the material. For example, dentists oftentimes employ coupling agents such as silane to provide a bond between the inorganic filler particles in the resin matrix. Furthermore, an activator-initiator is necessary to polymerize the resin. Most dental composite materials are monomers that are aromatic or aliphatic acrylates. The most commonly used methacrylates in dental composites are bis-GMA, urethane dimethacrylate (UEDMA), and triethylene glycol dimethacrylate (TEGDMA) which polymarize by addition polymerization.

Historically composites were cured by chemically activated polymerization (often referred to as "self-curing") that had to be mixed. Disadvantages of self-curing composites include the presence of air bubbles resulting from the mixing process that inhibit polymerization and reduce control of the working time after the material has been mixed. Thus, a dentist was required to place the resin composite on the affected area of the tooth surface and shape the resin composite immediately following initiation of the polymerization phase. Accordingly, dentists employed a light source for activation of the initiator system. Advantageously, light cured materials allow the dentist to complete the placement and shaping of the composite before curing is initiated. Upon initiation, light curing generally requires only forty seconds of curing time to cure a two millimeter (mm) thick layer. In contrast, a chemically cured material requires several minutes to set.

Ultraviolet light cured composites have been replaced by visible light activating systems that have a greater ability to polymerize thicker increments up to two millimeters (mm). Light curable dental composites are typically supplied in a paste or gel form contained in a syringe. The free radical initiating system, consisting of the photo initiator molecule and an amine activator, is contained in the paste or gel. The two components do not interact until exposed to light capable of initiating polymerization. Exposure to light of the correct wavelength—approximately 468 nanometers (nm)—produces an excited state of the photoinitiator and an interaction with the amine to form free radicals that initiate addition polymerization. In visible light cured dental restorations, amines such as camphorquinone and dimethylaminoethylmethacrylate generate free radicals when irradiated by visible light. Modern light sources are provided by handheld devices that contain a light source and typically include a short rigid light guide made up of fused optical fibers. Preferred light sources usually include a tungsten-halogen light bulb.

Light activated materials provide a number of advantages over chemically activated resins. The light curable resins are single component pastes that require no mixing, thus the dentist controls the working time. Further, materials harden rapidly upon exposure to the curing light. Because the depth of cure depends on several variables (e.g., material and the location and quality of the light source), the restoration must be built up incrementally within each cavity. In other words, each increment must be cured before applying the next layer of resin. This stepwise procedure translates into an advantage in resin-composite restoration because a significant portion of the polymerization shrinkage is compensated for as the cavities being filled are cured.

Because a typical dentist's operatory lights emit radiation in the 400 to 500 nm range (i.e., sufficient to initiate polymerization of the resin-composite material), a dentist will not dispense the resin until it is to be used. Dentists use a number of applicator tools to insert the resin into the cavity. For example, dentists typically use a syringe that is separate and apart from the individual applicators for dispensing etchant, water, air, and light source. In brief, the goal is to minimize deformation of the resin during application. The dentist shapes the resin in the desired form and then cures the resulting incremental layer once each increment is inserted. Thereafter, additional increments are added, shaped, and cured.

Modern industry provides dentists with a variety of tools for performing dental restorations. The particular tool selected by the dentist is dependent upon the dental procedure. For example, a common dental tool is a multi-purpose syringe for dispensing various types of dental materials (e.g., anesthesia, resins, impression material, and epoxies.) Another common dental tool is an air and water syringe for delivering air, water and an air-water mix to an affected tooth during restoration. Yet another common dental tool is a fiber optic handpiece which incorporates a fiber optic handle and light source to facilitate illumination of the oral cavity and to cure light curable composites. Nevertheless, the above-referenced handpieces and syringes are generally separate units that must be manipulated by the dentist. Stated differently, the conventional handpieces and syringes must be stored on a storage rack, and retrieved separately each time the dentist begins a different step of the restoration procedure. The time between the removal of the handpiece or syringe from the proximity of the patient's mouth, the placement of the syringe upon the storage rack, the retrieval of a different syringe, and the placement of new tools proximate the patient's mouth for the next step is critical during restorative procedures. As discussed above, it is common for a patient to use his tongue to wet his mouth—and affected area—when the dentist removes a dental tool from the patient's mouth. Despite the use of suction devices, the accumulation of moisture on the affected area degrades the structural integrity of the resin and results in a poor quality filling that is prone to failure. It is understood by those skilled in the art that the variety of available handpieces and syringes, specifically directed to individual tasks (e.g., etching, rinsing, and curing), fail to promote the rapid etching and restoration of a tooth, thereby leading to contamination and poor bonding between tooth and resin.

Various connectors are used for connecting conduits for air, water, and power in a handpiece or syringe to supply the hoses of an instrument delivery unit. There are four types of standard connectors used in the United States. The connectors include the two-hole (commonly referred to as a "Borden connector"), a three-hole, and a four-hole connector. The four-hole connector (commonly referred to as a "Midwest connector") is the most popular connector. In a four-hole connector, the holes are for drive air, chip air, water, and exhaust. A five-hole connector is also available wherein the fifth hole represents a fiber optic bundle. For standardization purposes, hole locations are determined by an International Standards Organization (ISO) specification. The Borden two-hole connector supplies compressed air through the larger of the two holes and cold water through the smaller. The Midwest design has an exhaust tube for removing spent air and provides spray air and water separately. Many variations of these two main designs exist, for example, to supply electricity to motors or supply light to the fiber optics system of a hand piece. Most hand pieces are configured to allow rotation between hand piece and the connector in order to prevent the rubber supply hose from twisting the instrument during normal use. Most dentists prefer to use a handpiece attachment or fitting (commonly referred to as "a quick disconnect") designed to allow easy separation of the handpiece from supply tubing. Dentists prefer the handpiece and "quick disconnect" combination because sterilization of all handpieces and syringes between patients has become standard practice. Nevertheless, the individual dental tools for etching, rinsing, and curing fail to take advantage of the quick disconnect system. This lack of multifunction dental tools ignores the reality that most dentists prefer a single handpiece or syringe that can be transported from room to room.

The majority of all light activated materials used in restoration procedures are activated by blue light as opposed to ultraviolet light. Modern light curing devices generally utilize a fiber optic bundle which consists of many hundreds of fine glass optic fibers wherein each fiber is constructed from a fine core of glass surrounded by an envelope of glass of a different retracted index. Light traveling within the core bounces off the walls of the fiber and back into the core by total internal reflection. The light only leaves the bundle when it reaches the cut end surface of the core. Conventional light sources include a tungsten-halogen bulb placed into a separate and larger hand piece that shines the light via a short rigid light guide into the mouth onto the surface of the light activated material. The output of the light decreases according to the inverse square law. Accordingly, a short length fiber optic glass bundle is preferred because doubling the distance from the glass bundle will quarter the light density.

Nevertheless, the conventional handpieces and syringes described above fail to provide an integrated syringe for expediting the delivery of dental material, air, water, and light to the tooth structure during the restorative procedures. In particular, the conventional syringes either provide only air and water or only dental material. Furthermore, most light sources are independent of the dental material delivery instrument. In other words, the dentists must resort to at least two or three different instruments during a procedure, thus prolonging the contamination period of an etched tooth. Increased contamination equates to weak bonds between the resin and the tooth structure, thus leading to further decay or staining of the tooth. Therefore, there is a need for a syringe for enhancing the bonding of restorative materials to the tooth structure.

Therefore, there is also a need for a means for expediting the delivery of dental material, water, air, and curing light to the affected tooth structure in order to minimize contamination of the etched area.

Further still, there is a need for a single syringe containing a plurality of reservoirs for retaining various dental materials integral with means for delivering air, water, and curing light.

OBJECT AND SUMMARY OF THE INVENTION

It is therefore an object of the present invention to provide for the restoration of teeth such that the bonding of restorative materials to the tooth structure is enhanced.

Another object of the invention is the provision of delivering etchant resin, water, air, and curing light via a single syringe to expedite the delivery of the same to the affected tooth structure such that contamination of the etched tooth is minimized.

A further object of the invention is the provision of a plurality of reservoirs within the hand-piece for containing etchant and resin to eliminate the need for multiple syringes for restoring and repairing a tooth structure.

The invention meets these objectives with a multifunction syringe for delivering dental material (e.g., etchant and resin), water, air, and light via a single hand-held unit. In particular, the invention is a syringe having a grip, body, and shank portion, a plurality of reservoirs for containing various dental materials within the body portion, tubing and channels for delivering air and water, and a light source for curing resin. The grip portion includes a trigger switch for activating the light source and a connector for connecting the syringe to an external instrument delivery system capable of delivering air, water, and power. The body of the syringe includes actuators for promoting the delivery of the dental material, air, and water. Advantageously, the integrated delivery of dental material, water, air, and curing light from a single syringe minimizes the contamination period affecting the etched tooth structure—thereby enhancing the structural bond between tooth and resin—because the syringe remains proximate the mouth cavity during the entire restorative procedure.

The foregoing and other objects and advantages of the invention and the manner in which the same are accomplished will become clearer based on the following detailed description taken in conjunction with the accompanying drawings in which:

BRIEF DESCRIPTION OF THE DRAWINGS

FIG. 1 is a top plan view of the multifunction syringe embodying the invention illustrating the grip, housing, and shank portion and further illustrating the actuator buttons of the preferred embodiment;

FIG. 2 is a side sectional view taken generally along lines 2—2 of FIG. 1 illustrating the reservoirs for containing dental material;

FIG. 3 is a cross-sectional view taken generally along lines 3—3 on FIG. 2 depicting conduits for supplying air, water, and electricity from an external instrument delivery system to the syringe defined by a connector for releasably connecting the syringe to supply hoses of the external instrument delivery system;

FIG. 4 is a cross-sectional view taken generally along lines 4—4 on FIG. 2 depicting the nozzle of the shank and the outlets for dental material, water, air, and a light source;

FIG. 5 is an enlarged end sectional view taken generally along lines 5—5 on FIG. 1 depicting an upper portion of the body and grip portion;

DETAILED DESCRIPTION OF THE INVENTION

Figure 7:
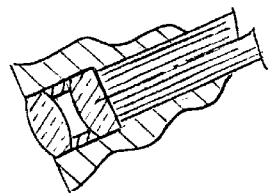
FIG. 7 is an enlarged partial sectional view of the distal end of the shank of FIG. 6 illustrating the fiber optic lens and fiber optic bundle.

The present invention will now be described more fully hereinafter with reference to the accompanying drawings, in which a preferred embodiment of the invention is shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

An overall view of the dental syringe which incorporates features of the present invention is set forth in FIG. 2. As used herein, the designation "instrument delivery system" refers to any conventional dental unit capable of conveying air, water, and a power supply to a handpiece or syringe.

As illustrated in FIG. 1, the dental syringe is comprised of a main body 10, a shank portion 11, and a grip portion 12. The grip portion 12 of the syringe is connected to supply hoses 13 of an external instrument delivery system by a conventional connector 14, commonly referred to as a "quick disconnect" in the dental field (see FIG. 2). The quick disconnect 14 is typically secured to a dental syringe by a ball detent mechanism or a spring-tension dog clutch. The dental syringe is preferably formed of metal or similar hard material having sufficient strength to withstand conventional sterilization procedures using superheated steam under high pressure, typically performed in an autoclave.

As illustrated in FIG. 2, the body 10 of the syringe supports a dental material delivery means comprised of a plurality of reservoirs 15, a plurality of dental material passageways 20, and pressure actuated diaphragms 21. The dental material delivery means conveys dental material contained in the reservoirs 15 to a nozzle 22 defined by a distal end of the shank portion 11. The dental material passageways 20 defined by the shank 11 have an upstream end in fluid communication with the reservoirs 15 and a downstream end that defines at least two outlets in the nozzle 23. Accordingly, the syringe is capable of delivering at least two separate types of dental material such as an etchant for etching portions of a tooth structure and a resin or resin composite for restoring the tooth structure. The pressure actuated diaphragms 21 are positioned adjacent an end 24 of each reservoir 15 in fluid communication with an air distribution means. Thus, the air distribution means is capable of urging dental material from the reservoirs 15 along the dental material passageways 20 and out of the dental material outlets 23 (depicted as E for etchant and R for resin in FIG. 4) on the nozzle 22. As shown in FIG. 5, each reservoir 15 includes a fill hole 25 providing access to the reservoirs 15 such that an operator can readily inject dental material into the reservoir. The fill holes 25 may be covered by any type of plugging means for retaining the dental material in the reservoir 15 during the normal handling of the syringe. In the preferred embodiment, a cap screw 30 is depicted in FIGS. 2 and 5. It will be understood, however, that the plugging means may include a resilient stopper or plug of sufficient strength to seal the fill hole. Advantageously, the fill holes 25 allow an operator to easily clean the reservoirs 15, dental material passageway 20, and outlets 23 by flushing the dental syringe with an appropriate cleaning solution (e.g., an acetone based liquid or water).

Figure 8:
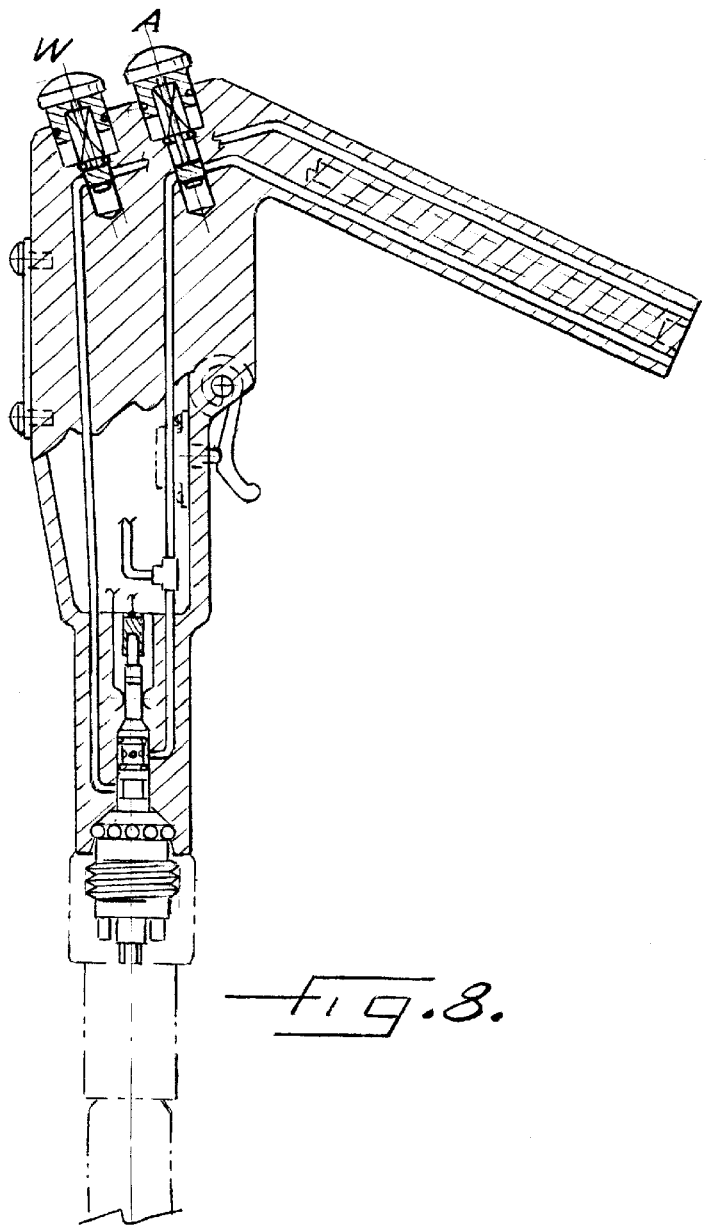
FIG. 8 is a side sectional view taken generally along lines 8—8 on FIG. 1 illustrating the air and water tubing, air and water actuators, and air and water channels.

As depicted in FIGS. 2 and 8, the dental syringe further comprises an air distribution means comprised of an air channel 31, air tubing 32, a manifold 33, and regulator 34. The air channel 31 extends the length of the shank 11 and has an upstream end in fluid communication with the air tubing 32 and a downstream end defining an air outlet 40 on the nozzle (depicted as A for air in FIG. 4). The air tubing 32 extends the length of the body 10 and grip 12 portion of the syringe and has an upstream end in fluid communication with an external air source and a downstream end in fluid communication with each pressure actuated diaphragm 21. The manifold 33 is disposed in the syringe intermediate to the external air source and the reservoirs 15 for directing external air under pressure against the pressure actuated diaphragms 21. The regulator 34 for regulating the external air traveling through the air tubing 32 is positioned intermediate to the manifold 33 and the reservoirs 15. The regulator 34 may be pre-set to provide sufficient air pressure to activate the diaphragm 21. Thus, the regulator 34 diverts external air to the nozzle 22 for drying an affected area of the tooth and against the pressure actuated diaphragm 21 for urging dental material to the nozzle 22 for restoring the tooth structure. Accordingly, the pressure actuated diaphragm 21 which is positioned to sealingly engage portions of the interior walls of the reservoirs 15 expands under increased air pressure delivered by the air tubing 32 against one side of the diaphragm 21 and urges dental material contained therein into the dental material passageway 20 in the shank 11 of the syringe. Upon entering the dental material passageway 20, the dental material is advanced out of the dental material outlets 23 on the nozzle 22 and onto the affected area of a tooth.

FIG. 8 also illustrates a water distribution means comprised of a water channel 44 extending the length of the shank 11 and water tubing 45 extending the length of the body 10 and grip 12 portion of the syringe. The water channel 44 in the shank portion has an upstream end in fluid communication with the water tubing 45 and a downstream end defining a water outlet 52 (depicted as W for water in FIG. 4) on the nozzle 22. The water tubing 45 has an upstream end in fluid communication with an external water source and a downstream end in fluid communication with the water channel 44. The preferred embodiment thus provides a stream of water for rinsing etchant from an etched area of the tooth structure.

As shown in FIG. 2, the dental syringe also includes an advancement means for advancing dental material, external air, and external water onto the tooth structure. The advancement means is comprised of a plurality of chambers 63, 64, 65, 70, pistons 56, 57, 58, 59, plungers 76, 77, 78, 79, and actuators 66, 67, 68, 72. In the preferred embodiment, the advancement means is comprised of a first and second chamber 63, 64 associated with the reservoirs 15, a first piston 56 and first plunger 76 associated with the first chamber 63, a second piston 56 and second plunger 77 associated with the second chamber 64, an etchant actuator 66 (depicted as E for etchant in FIGS. 1, 2, and 5) and resin actuator 67 (depicted as R for resin in FIGS. 1, 2 and 5) for advancing dental materials, a third chamber 65 associated with the air distribution means and an air actuator 68 (depicted as A for air in FIGS. 1, 2, and 5) for advancing air, a third piston 58 and third plunger 78 associated with the third chamber 65, a fourth chamber 70 associated with the water distribution means and a water actuator 72 (depicted as W for water in FIGS. 1, 2, and 5) for advancing water, and a fourth piston 59 and fourth plunger 79 associated with the fourth chamber 70. As used herein, the phrase "associated with" refers to the mechanical or pneumatic interaction between the respective parts of the present invention.

Each chamber 63, 64, 65, 70 is positioned intermediate to the reservoirs 15 in the body portion 10 and the shank 11. The first and second chambers 63, 64 have upstream ends in fluid communication with the reservoirs 15 and downstream ends in fluid communication with the dental material passageways 20. The first and second chambers 63, 64 are described consecutively because both first and second chambers operate to advance the flow of the dental material contained in the reservoirs 15. In contrast, the third and fourth chambers 65, 70 are described independent from one another because the third chamber operates to advance external air through the syringe body and the fourth chamber operates to advance external water through the syringe body. The first and second pistons 56, 57 are supported at one end by the etchant actuator 66 and the resin actuator 67, respectively, mounted externally to the syringe. In the preferred embodiment, the actuators 66, 67 are spring-mounted to the top of the syringe. Thus, the first and second chambers 63, 64 provide a passageway for the dental material to travel from the reservoirs 15 and into the shank 11. The first and second pistons 56, 57 are mounted to reciprocate into a portion of the first and second chambers 63, 64 and the reservoirs 15. The first and second plungers 76, 77 are attached to an opposite end of each first and second pistons 56, 57 and are positioned to seal an end of the reservoir 15 that is in fluid communication with the dental material passageways 20 in the shank 11. The first and second plungers 76, 77 are mounted to prevent the advancement of the dental material until the etchant and resin actuators 66, 67 are depressed.

In operation, the dental material contained within the reservoirs 15 is advanced through the first and second chambers 63, 64 into the dental material passageway 20 and out of the dental material outlets 23 onto a tooth structure when an operator depresses either actuator 66, 67 associated with the respective dental material reservoirs 15, thereby reciprocating the first and second pistons 56, 57 into the reservoirs 15 and creating a passageway for the dental material from the reservoirs to advance along the dental material passageways and out the outlets. Thus, the present invention provides a single syringe for delivering an etchant and a resin to the affected area of the tooth structure.

Specifically, when the actuators 66, 67 associated with the first and second chambers 63, 64 are depressed, the respective diaphragm 21 expands into the reservoir 15 under pressure provided by the pressurized air from an external air source and into the dental syringe by way of the air tubing 32. When the actuators 66, 67 are depressed, the first and second pistons 56, 57 reciprocate the first and second plungers 76, 77 into the reservoirs 15 thereby promoting the flow of the dental material from the reservoirs through the first 63 and second 64 chambers and into the passageways 20 defined by the shank 11 portion of the syringe, eventually exiting the nozzle 22 at the dental material outlets 23. The regulating valve 34 positioned intermediate to the reservoirs 15 and the manifold 33 is pre-set to ensure low-pressure air is delivered to the diaphragm 21 and thus provides a sufficient amount of air pressure to deliver a steady flow of the dental material from the reservoir and into the dental material passageways 20 when the actuators 66, 67 are depressed.

The third chamber 65 of the advancement means associated with the air distribution means likewise includes a third piston 58, a third plunger 78, and an air actuator 68 as depicted in FIG. 8. The third chamber 65 has an upstream end in fluid communication with the air tubing 32 and a downstream end in fluid communication with the air channel 31 in the shank 11. The third plunger 78 is attached to one end of the third piston 58 and is mounted to provide a seal between the air tubing 32 and the air channel 31 within the shank 11. The third piston 58 is supported at one end by the air actuator 68 mounted externally to the syringe. In the preferred embodiment illustrated in FIG. 8, the air actuator 68 is spring-mounted to an upper portion of the dental syringe. In operation, air is conveyed from an external air source through the body portion 10 and onto the affected area of a tooth when an operator depresses the air actuator 68, thereby reciprocating the third piston 58 into a portion of the chamber 65 and unseating the third plunger 78 from the end of the chamber in fluid communication with the air tubing 32. Operating in this fashion, air flows from the air tubing 32 into the air channel 31 and out of the air outlet 40 on the nozzle 22.

The fourth chamber 70 of the advancement means associated with the water distribution means likewise includes a fourth piston 59, a fourth plunger 79, and a water actuator 72 (see FIG. 8). The fourth chamber 70 has an upstream end in fluid communication with the water tubing 45 and a downstream end in fluid communication with the water channel 44 in the shank 11. The fourth plunger 79 is attached to one end of the fourth piston 59 and is mounted to provide a seal between the water tubing 45 and the water channel 44 within the shank 1. The piston is supported at one end by the water actuator 72 mounted externally to the syringe. In the preferred embodiment illustrated in FIG. 8, the water actuator 72 is spring-mounted to an upper portion of the dental syringe. In operation, water is conveyed from an external water source through the body portion 10 and onto the affected area of a tooth when an operator depresses the water actuator 72, thereby reciprocating the piston 59 into a portion of the chamber 70 and unseating the plunger 79 from the end of the chamber in fluid communication with the water tubing 45. Accordingly, water flows from the water tubing 45 into the water channel 44 and out of the water outlet 52 on the nozzle 22.

As shown in FIG. 4, the nozzle includes two dental material outlets 23, the air outlet 40, and the water outlet 52 positioned in spaced relationship to one another. This configuration provides sufficient separation of the outlets for unobstructed delivery of the dental material, air, and water to the mouth cavity.

Figure 6:
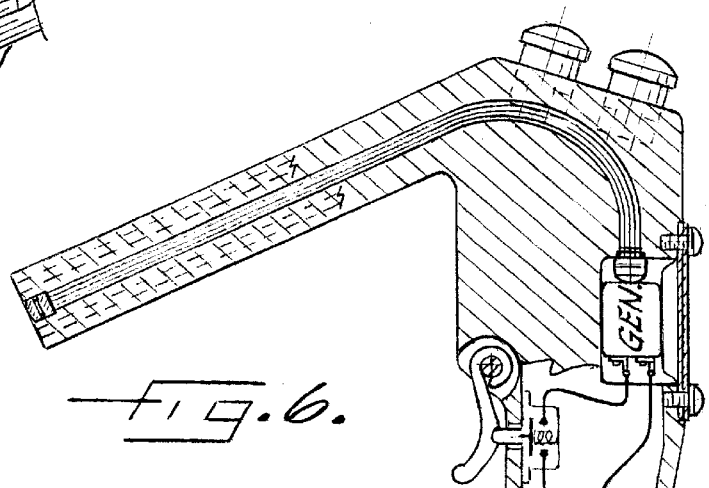
FIG. 6 is a side sectional view of the present invention taken generally along lines 6—6 on FIG. 1 depicting the fiber optics assembly contained within the syringe.

A preferred embodiment of the present invention as depicted in FIG. 6 is further comprised of a light source 73 and a light transmitting means contained within the syringe.

The light source may be a visible, ultraviolet, infrared, or laser depending upon the type of resin or dental restorative composite material to be cured. The light source 73 (depicted as GEN, for generating source in FIG. 6) includes a transformer, a voltage stabilizer, a timing circuit, cooling fan motor, and a cooling air outlet. A bulb 75 and filter 80 are positioned adjacent the light source 73 for transmitting and filtering the light, respectively. Access to the light source 73 is provided by an opening 81 in the syringe adjacent the light source 73.

A cover plate 82 secured over the opening by conventional screws protects the light source 73 from external environmental factors (see FIGS. 2, 3, and 6). Electrical conduits 83 positioned within the syringe electrically connect the generating source 74 to an external power source (depicted as power supply in FIG. 2). The light transmitting means is comprised of a bundle of fiber optic filaments 84 having one end adjacent the bulb 75 and filter 80 and an opposite end adjacent the nozzle 22 at the end of the shank 11. FIG. 7 illustrates a common fiber optic bundle 84 including an outer sheath 85 wrapped around flexible casing 90 which encloses a bundle of fibers. The nozzle 22 may also include a lens 91 at the end of the fiber optic bundle 84 for focusing the light transmitted via the fiber optic bundle onto the tooth structure. FIG. 4 illustrates the lens 91 positioned on the nozzle 22 surrounded by the dental material outlets 23, air outlet 40, and water outlet 52.

An alternative embodiment of the present invention (not shown) includes a light transmitting means comprised of a fiber optic bundle extending the length of the syringe and connected to an external light source. In this alternative preferred embodiment, the external light source embodies the generating source and likewise includes a voltage stabilizer, timing circuit, filter, transformer, and a cooling fan motor.

The preferred embodiment of the dental syringe also includes a light source activating means positioned on an external portion of the grip of the syringe for activating the light source. The light source activating means is comprised of a trigger switch 92 electrically connected to the light source 73 by the electrical conduits 83 within the syringe. It will be understood that the light activating means may include any conventional trigger switch button, lever, or the like capable of activating the light source 73. The trigger switch, button, or lever is positioned on the grip portion 12 of the syringe for easy manipulation by the operator. A switch 93 associated with the light source activating means for activating the light source is positioned adjacent the trigger switch within the syringe.

In the preferred alternative embodiment, the trigger switch 92 activates the external light source (not shown) and the fiber optic bundle 84 transmits the light from the external light source through the syringe and out of the nozzle 22 to irradiate the mouth cavity and cure the light-curable resin composite.

As illustrated in the FIG. 2, the dental syringe may be connected to a supply hose 13 from the instrument delivery system by a coupling means. The coupling means is associated with a lower portion of the syringe body 10 for detachably connecting the syringe to the supply hose 13 of an external instrument delivery system (not shown). The coupling means (or "quick disconnect") is comprised of a mount 94 positioned within a lower end of the grip portion 12 for receiving the connector 14. As shown in FIG. 3, the connector 14 includes an air conduit 100, water conduit 101, and a power conduit 102 for conveying air, water, and power from an external instrument delivery system and through conduits that are positioned to align with the air and water tubing and electrical conduits in the syringe when the male end of the connector 14 is inserted into a female member associated with the syringe body 10. Conventional connectors typically include a ball detent mechanism positioned around the periphery of an intermediate portion of the connector for releasably securing the connector and the syringe. FIG. 3 depicts a cross-sectional view of the connector taken along lines 3—3 and portrays a conventional four-hole connector. Conventional connectors include an alignment means (not shown) comprised of grooves and slots adapted to connect the air, water, and power conduits 100, 101, 102 of the connector 14 so that external air and water is in fluid communication with the air and water tubing 32, 45 in the syringe and the external power source is electrically connected to the electrical conduits 83 disposed within the syringe. In the preferred alternative embodiment, including an external light generating source, the connector includes a conduit 103 for connecting the fiber optic bundles 84 in the supply hose 13 and in the syringe (see FIG. 3).

In another preferred embodiment of the present invention (not shown), the syringe includes a detachable shank which can be removed for cleaning. The alternative embodiment is further comprised of an attachment means associated with the shank and the body portion for releasably attaching the shank to the body of the syringe. The attachment means may be comprised of a bayonet-type mount including a male member which defines at least one recessed groove about its circumference. A mating female member located in the downstream portion of the body includes corresponding studs. The operator can secure the shank to the body by inserting the male member into the downstream portion of the handle and rotating the shank or body until the studs are fully received by the recessed groove. An o-ring is positioned about the circumference of upstream portion of the male member and provides a seal for the connection between the shank and the body. One-way diaphragm valves may be positioned in a portion of the dental material passageways for preventing the dental material in the shank from flowing back into the unused portion of the dental material contained in the plurality of reservoirs.

In another preferred embodiment, the shank of the syringe may be secured to the body by alternatively threaded male and female members with corresponding stops and helically aligned threads which, when fully tightened, will cause the dental material passageways, air distribution means, water distribution means, and light transmitting means to be in communication with each other. This alternative embodiment of the present invention includes attachment means configured to always align the shank when attached to the body so that the dental material, air, water, and light can be delivered. Such attachment means may include any number of threaded members and associated stops or a bayonet-type mount and associated studs.

From the foregoing, it will be seen that there has been brought to the art a new device which overcomes the drawbacks of restoring a tooth structure with multiple dental instruments. A particular advantage of the present invention is the dentist's ability to use a single dental instrument for delivering dental material, air, water, and curing light to an affected area of the tooth structure such that the syringe is proximate the patient's mouth during the entire restorative procedure. In other words, the dentist can etch the tooth, flush the etched area with water, dry the affected area with air, extrude resin onto the affected area, and immediately cure the resin with light without removing the syringe from the mouth cavity. The rapid succession of the restorative steps minimizes the contamination of the etched tooth structure, thereby enhancing the bond between the enamel or dentin of the tooth structure and the resin. An additional advantageous aspect of the invention is the elimination of the necessity of multiple dental instruments and the delays associated with the retrieval and replacement of the same.

In the drawings and specification, there have been disclosed typical embodiments on the invention and, although specific terms have been employed, they have been used in a generic and descriptive sense only and not for purposes of limitation, the scope of the invention being set forth in the following claims.

That which is claimed is:

1. A multifunction dental syringe for use in dental restorative procedures in conjunction with conventional instrument delivery systems, said syringe comprising:
   a body having a grip portion and shank portion;
   a dental material delivery means disposed within said body for conveying dental material from a plurality of reservoirs disposed within said body to a nozzle defined by a distal end of said shank portion;
   an air distribution means disposed within said body for conveying external source air to said nozzle;
   a water distribution means disposed within said body for conveying external source water to said nozzle; and
   an advancement means disposed within said body for advancing dental material from said plurality of reservoirs and external source air and water from said air and water distribution means to said nozzle.

2. A multifunction dental syringe according to claim 1, wherein said dental material delivery means comprises a plurality of passageways defined by said shank having an upstream end in fluid communication with said plurality of reservoirs and a downstream end defining at least two outlets in said nozzle.

3. A multifunction dental syringe according to claim 1, wherein said dental material delivery means further comprises a pressure actuated diaphragm positioned to sealingly engage interior walls of said reservoirs and in fluid communication with said air distribution means for urging dental material from said reservoirs along said dental material passageways and out said at least two outlets on said nozzle.

4. A multifunction dental syringe according to claim 1, wherein said air distribution means comprises an air channel defined by said shank having an upstream end in fluid communication with air tubing disposed within said body and a downstream end defining an air outlet in said nozzle.

5. A multifunction dental syringe according to claim 1, wherein said air distribution means further comprises a manifold disposed within said body and positioned intermediate to an external air source and said reservoirs for directing external air under pressure against said pressure actuated diaphragm.

6. A multifunction dental syringe according to claim 5, wherein said air-distribution means further comprises a regulator for regulating external air positioned intermediate said manifold and said reservoirs.

7. A multifunction dental syringe according to claim 1, wherein said water distribution means comprises a water channel defined by said shank having an upstream end in fluid communication with water tubing disposed within said body and a downstream end defining a water outlet in said nozzle.

8. A multifunction dental syringe according to claim 1, wherein said advancement means comprises
   a first and second chamber disposed within said body and associated with said dental delivery means and said air distribution means;
   a third chamber disposed within said body and associated with said air distribution means; and
   a fourth chamber disposed within said body and associated with said water distribution means.

9. A multifunction dental syringe according to claim 8, wherein said advancement means further comprises
   a piston associated with each of said first and second chambers for reciprocating into at least a portion of said first and second chamber and said reservoirs;
   a plunger associated with each of said first and second chambers attached to one end of said piston and positioned in sealing engagement with said interior walls of said reservoirs;
   an actuator associated with each of said first and second chambers attached to an opposite end of said piston; and
   wherein dental material is advanced from said reservoirs into said dental material passageways and out said at least two dental material outlets in said nozzle when said actuator is depressed and said pressure actuated diaphragm expands into said reservoir under pressure provided by said air distribution means.

10. A multifunction dental syringe according to claim 8, wherein said advancement means further comprises
    a piston associated with each of said third and fourth chambers for reciprocating into at least a portion of said third and fourth chambers;
    a plunger associated with each of said third and fourth chambers and mounted in sealing engagement with interior walls of said third and fourth chambers;
    an actuator associated with each of said third and fourth chambers and attached to an opposite end of said piston; and
    wherein external air and water is advanced through said air and water tubing and out said air and water outlets when said actuator is depressed.

11. A multifunction dental syringe according to claim 1, further comprising a light source and a light transmitting means integral with said body for conveying light from said light source to said nozzle.

12. A multifunction dental syringe according to claim 11, wherein said light source is disposed within said body.

13. A multifunction dental syringe according to claim 11, wherein said light source is external to said body.

14. A multifunction dental syringe according to claim 11, wherein said light source includes a visible light source capable of curing dental restorative material.

15. A multifunction dental syringe according to claim 11, wherein said light transmitting means comprises a plurality of fiber optic filaments having one end adjacent said light source and an opposite end adjacent said nozzle.

16. A multifunction dental syringe according to claim 11, wherein said light transmitting means is disposed within said body.

17. A multifunction dental syringe according to claim 11, further comprising a light source activating means positioned on said grip portion of said syringe for activating and deactivating said light source.

18. A multifunction syringe according to claim 17, wherein said light source activating means comprises a lever electrically connected to said light source by electrical conduits disposed within said syringe.

19. A multifunction syringe according to claim 17, wherein said light source activating means further comprises a button electrically connected to said light source by electrical conduits disposed within said syringe.

20. A multifunction dental syringe according to claim 1, further comprising a coupling means associated with said grip portion for detachably connecting said syringe to supply hoses of an external instrument delivery system.

21. A multifunction dental syringe according to claim 20, wherein said coupling means comprises a mount integral with said grip portion for receiving a connector, said connector having conduits for conveying air, water, and power from an external instrument delivery system such that said air and water conduits are in fluid communication with said air and water tubing in said body and said power conduit is electrically connected to said electrical conduits disposed within said body.

22. A multifunction dental syringe according to claim 1, wherein said body portion defines a plurality of fill holes adjacent said plurality of reservoirs for providing access to said reservoirs, said fill holes adapted to engage a sealing means for retaining dental material in said reservoirs.

23. A multifunction dental syringe according to claim 22, wherein said sealing means comprises a cap screw.

24. A multifunction dental syringe according to claim 22, wherein said sealing means further comprises a stopper of sufficient strength to retain dental material in said reservoirs.

25. A multifunction dental syringe according to claim 1, wherein said shank is removable, and further comprising an attachment means disposed within said body and associated with said shank and said body for removably attaching said shank to said body, said shank defining a plurality of passageways having an upstream end in fluid communication with said dental material delivery means, said air distribution means, and said water distribution means, and a downstream end defining at least one opening in said shank.

26. A multifunction dental syringe according to claim 25, wherein said attachment means comprises a bayonet-type mount including a male member defining at least one recessed groove about its circumference and mounted on said shank and a female member in said body including a stud for being received in said groove for securing said male member to said body.

27. A multifunction dental syringe according to claim 26, wherein said attachment means further comprises an o-ring seal for sealing the connection between said male and female members.

28. A multifunction dental syringe according to claim 25, wherein said attachment means further comprises threads and a stop on said shank and corresponding threads and a stop on said body, said threads and stops being helically aligned with said shank and said body such that said body and said shank are in fluid communication when said threads are fully tightened and said stops engage each other.

29. A multifunction dental syringe for use in dental restorative procedures in conjunction with conventional instrument delivery systems, said syringe comprising:
   a body having a grip portion and shank portion;
   a plurality of passageways defined by said shank for conveying dental material from a plurality of reservoirs disposed within said body to a nozzle defined by a distal end of said shank portion, said dental material passageways having an upstream end in fluid communication with said reservoirs and a downstream end defining at least two outlets in said nozzle;
   a water channel defined by said shank having an upstream end in fluid communication with water tubing disposed within said body and a downstream end defining a water outlet in said nozzle.
   a pressure actuated diaphragm positioned to adjacent interior walls of said reservoirs in fluid communication with an air channel defined by said shank for urging dental material from said reservoirs along said dental material passageways and out said at least two outlets on said nozzle; said air channel having an upstream end in fluid communication with air tubing disposed within said body and a downstream end defining an air outlet in said nozzle;
   a manifold disposed within said body and positioned intermediate to an external air source and said reservoirs for directing external air under pressure against said pressure actuated diaphragm;
   a regulator for regulating external air positioned intermediate said manifold and said reservoirs;
   an actuator disposed within said body for advancing dental material from said plurality of reservoirs and external source air and water from said air and water tubing to said nozzle.

30. A multifunction dental syringe according to claim 29, wherein said actuator further comprises
   a first and second chamber disposed within said body for advancing dental material from said plurality of reservoirs to said nozzle;
   a third chamber disposed within said body for advancing air from said air tubing to said air outlet; and
   a fourth chamber disposed within said body for advancing water from said water tubing to said water outlet.

31. A multifunction dental syringe according to claim 30, wherein said actuator further comprises
   a piston associated with each of said first and second chambers for reciprocating into at least a portion of said first and second chamber and said reservoirs;
   a plunger associated with each of said first and second chambers attached to one end of said piston and positioned in sealing engagement with said interior walls of said reservoirs;
   an actuator associated with each of said first and second chambers attached to an opposite end of said piston; and
   wherein dental material is advanced from said reservoirs into said dental material passageways and out said at least two dental material outlets in said nozzle when said actuator is depressed and said pressure actuated diaphragm expands into said reservoir under pressure provided by said air distribution means.

32. A multifunction dental syringe according to claim 30, wherein said actuator further comprises
   a piston associated with each of said third and fourth chambers for reciprocating into at least a portion of said third and fourth chambers;
   a plunger associated with each of said third and fourth chambers and mounted in sealing engagement with interior walls of said third and fourth chambers;
   an actuator associated with each of said third and fourth chambers and attached to an opposite end of said piston; and
   wherein external air and water is advanced through said air and water tubing and out said air and water outlets when said actuator is depressed.

33. A multifunction dental syringe according to claim 29, further comprising a light source and a plurality of fiber optic filaments disposed within said body having, one end adjacent said light source and an opposite end adjacent said nozzle for conveying light from said light source to said nozzle.

34. A multifunction dental syringe according to claim 33, wherein said light source is disposed within said body.

35. A multifunction dental syringe according to claim 33, wherein said light source is external to said body.

36. A multifunction dental syringe according to claim 33, wherein said light source includes a visible light source capable of curing dental restorative material.

37. A multifunction dental syringe according to claim 33, further comprising a light source activator positioned on said grip portion of said syringe for activating and deactivating said light sources.

38. A multifunction syringe according to claim 37, wherein said light source activator is a lever electrically connected to said light source by electrical conduits disposed within said syringe.

39. A multifunction syringe according to claim 37, wherein said light source activator is a button electrically connected to said light source by electrical conduits disposed within said syringe.

40. A multifunction dental syringe according to claim 29, further comprising a coupling associated with said grip portion for detachably connecting said syringe to supply hoses of an external instrument delivery system.

41. A multifunction dental syringe according to claim 40, wherein said coupling includes a mount integral with said grip portion for receiving a connector, said connector having conduits for conveying air, water, and power from an external instrument delivery system such that said air and water conduits are in fluid communication with said air and water tubing in said body and said power conduit is electrically connected to said electrical conduits disposed within said body.

42. A multifunction dental syringe according to claim 29, wherein said body portion defines a plurality of fill holes adjacent said plurality of reservoirs for providing access to said reservoirs, said fill holes adapted to engage a sealing means for retaining dental material in said reservoirs.

43. A multifunction dental syringe according to claim 42, wherein said sealing means comprises a cap screw.

44. A multifunction dental syringe according to claim 42, wherein said sealing means further comprises a stopper of sufficient strength to retain dental material in said reservoirs.

45. A multifunction dental syringe for use in dental restorative procedures in conjunction with conventional instrument delivery systems, said syringe comprising:
   a body having a grip portion;
   a dental material delivery means disposed within said body for conveying dental material from a plurality of reservoirs disposed within said body to a removably attached shank;
   an attachment means disposed within said body and associated with said shank and said body for removably attaching said shank to said body;
   an air distribution means disposed within said body for conveying external source air to said shank;
   a water distribution means disposed within said body for conveying external source water to said shank; and
   an advancement means disposed within said body for advancing dental material from said plurality of reservoirs and external source air and water from said air and water distribution means to said shank;
   wherein said shank defines a plurality of passageways having an upstream end in fluid communication with said dental material delivery means, said air distribution means, and said water distribution means, and a downstream end defining at least one opening in said shank.

46. A multifunction dental syringe according to claim 45, wherein said attachment means comprises a bayonet-type mount including a male member defining at least one recessed groove about its circumference and mounted on said shank and a female member in said body including a stud for being received in said groove for securing said male member to said body.

47. A multifunction dental syringe according to claim 45, wherein said attachment means further comprises an o-ring seal for sealing the connection between said male and female members.

48. A multifunction dental syringe according to claim 45, wherein said attachment means comprises threads and a stop on said shank and corresponding threads and a stop on said body, said threads and stops being helically aligned with said shank and said body such that said body and said shank are in fluid communication when said threads are fully tightened and said stops engage each other.

49. A multifunction dental syringe according to claim 45, wherein said dental material delivery means comprises a plurality of passageways defined by said shank having an upstream end in fluid communication with said plurality of reservoirs and a downstream end defining at least two outlets in said nozzle.

50. A multifunction dental syringe according to claim 45, wherein said dental material delivery means further comprises a pressure actuated diaphragm positioned to sealingly engage interior walls of said reservoirs and in fluid communication with said air distribution means for urging dental material from said reservoirs along said dental material passageways and out said at least two outlets on said nozzle.

51. A multifunction dental syringe according to claim 45, wherein said air distribution means comprises an air channel defined by said shank having an upstream end in fluid communication with air tubing disposed within said body and a downstream end defining an air outlet in said nozzle.

52. A multifunction dental syringe according to claim 45, wherein said air distribution means further comprises a manifold disposed within said body and positioned intermediate to an external air source and said reservoirs for directing external air under pressure against said pressure actuated diaphragm.

53. A multifunction dental syringe according to claim 52, wherein said air distribution means further comprises a regulating means for regulating external air positioned intermediate said manifold and said reservoirs.

54. A multifunction dental syringe according to claim 45, wherein said water distribution means comprises a water channel defined by said shank having an upstream end in fluid communication with water tubing disposed within said body and a downstream end defining a water outlet in said nozzle.

55. A multifunction dental syringe according to claim 45, wherein said advancement means comprises
   a first and second chamber disposed within said body and associated with said dental delivery means and said air distribution means;
   a third chamber disposed within said body and associated with said air distribution means; and
   a fourth chamber disposed within said body and associated with said water distribution means.

56. A multifunction dental syringe according to claim 55, wherein said advancement means further comprises
   a piston associated with each of said first and second chambers for reciprocating into at least a portion of said first and second chamber and said reservoirs;
   a plunger associated with each of said first and second chambers attached to one end of said piston and positioned in sealing engagement with said interior walls of said reservoirs;

an actuator associated with each of said first and second chambers attached to an opposite end of said piston; and wherein dental material is advanced from said reservoirs into said dental material passageways and out said at least two dental material outlets in said nozzle when said actuator is depressed and said pressure actuated diaphragm expands into said reservoir under pressure provided by said air distribution means.

57. A multifunction dental syringe according to claim 55, wherein said advancement means further comprises a piston associated with each of said third and fourth chambers for reciprocating into at least a portion of said third and fourth chambers;

a plunger associated with each of said third and fourth chambers and mounted in sealing engagement with interior walls of said third and fourth chambers;

an actuator associated with each of said third and fourth chambers and attached to an opposite end of said piston; and wherein external air and water is advanced through said air and water tubing and out said air and water outlets when said actuator is depressed.

58. A multifunction dental syringe according to claim 45, further comprising a light source and a light transmitting means for conveying light from said light source to said nozzle.

59. A multifunction dental syringe according to claim 58, wherein said light source is disposed within said body.

60. A multifunction dental syringe according to claim 58, wherein said light source is external to said body.

61. A multifunction dental syringe according to claim 58, wherein said light source includes a visible light source capable of curing dental restorative material.

62. A multifunction dental syringe according to claim 58, wherein said light transmitting means comprises a plurality of fiber optic filaments having one end adjacent said light source and an opposite end adjacent said nozzle.

63. A multifunction dental syringe according to claim 58, wherein said light transmitting means is disposed within said body.

64. A multifunction dental syringe according to claim 58, further comprising a light source activating means positioned on said grip portion of said syringe for activating and deactivating said light source.

65. A multifunction syringe according to claim 64, wherein said light source activating means comprises a lever electrically connected to said light source by electrical conduits disposed within said syringe.

66. A multifunction syringe according to claim 64, wherein said light source activating means further comprises a button electrically connected to said light source by electrical conduits disposed within said syringe.

67. A multifunction dental syringe according to claim 45, further comprising a coupling means associated with said grip portion for detachably connecting said syringe to supply hoses of an external instrument delivery system.

68. A multifunction dental syringe according to claim 67, wherein said coupling means comprises a mount integral with said grip portion for receiving a connector, said connector having conduits for conveying air, water, and power from an external instrument delivery system such that said air and water conduits are in fluid communication with said air and water tubing in said body and said power conduit is electrically connected to said electrical conduits disposed within said body.

69. A multifunction dental syringe according to claim 45, wherein said body portion defines a plurality of fill holes adjacent said plurality of reservoirs for providing access to said reservoirs, said fill holes adapted to engage a sealing means for retaining dental material in said reservoirs.

70. A multifunction dental syringe according to claim 69, wherein said sealing means comprises a cap screw.

71. A multifunction dental syringe according to claim 69, wherein said sealing means further comprises a stopper of sufficient strength to retain dental material in said reservoirs.

72. A multifunction dental syringe for use in dental restorative procedures in conjunction with conventional instrument delivery systems, said syringe comprising:

a body having a grip portion;

a dental material delivery means disposed within said body for conveying dental material from a plurality of reservoirs disposed within said body to a removably attached shank;

an attachment means disposed within said body and associated with said shank and said body for removably attaching said shank to said body;

an air distribution means disposed within said body for conveying external source air to said shank;

a water distribution means disposed within said body for conveying external source water to said shank; and an advancement means disposed within said body for advancing dental material from said plurality of reservoirs and external source air and water from said air and water distribution means to said shank; and a light transmitting means disposed within said body for conveying light from an external light source to said nozzle;

wherein said shank defines a plurality of passageways having an upstream end in fluid communication with said dental material delivery means, said air distribution means, and said water distribution means, and a downstream end defining at least one opening in said shank.

73. A multifunction dental syringe according to claim 72, wherein said attachment means comprises a bayonet-type mount including a male member defining at least one recessed groove about its circumference and mounted on said shank and a female member in said body including a stud for being received in said groove for securing said male member to said body.

74. A multifunction dental syringe according to claim 73, wherein said attachment means further comprises an o-ring seal for sealing the connection between said male and female members.

75. A multifunction dental syringe according to claim 72, wherein said attachment means further comprises threads and a stop on said shank and corresponding threads and a stop on said body, said threads and stops being helically aligned with said shank and said body such that said body and said shank are in fluid and electrical communication and when said threads are fully tightened and said stops engage each other.

76. A multifunction dental syringe according to claim 72, wherein said dental material delivery means comprises a plurality of passageways defined by said shank having an upstream end in fluid communication with said plurality of reservoirs and a downstream end defining at least two outlets in said nozzle.

77. A multifunction dental syringe according to claim 72, wherein said dental material delivery means further comprises a pressure actuated diaphragm positioned to sealingly engage interior walls of said reservoirs and in fluid communication with said air distribution means for urging dental material from said reservoirs along said dental material passageways and out said at least two outlets on said nozzle.

78. A multifunction dental syringe according to claim 72, wherein said air distribution means comprises an air channel defined by said shank having an upstream end in fluid communication with air tubing disposed within said body and a downstream end defining an air outlet in said nozzle.

79. A multifunction dental syringe according to claim 72, wherein said air distribution means further comprises a manifold disposed within said body and positioned intermediate to an external air source and said reservoirs for directing external air under pressure against said pressure actuated diaphragm.

80. A multifunction dental syringe according to claim 72, wherein said air distribution means further comprises a regulating means for regulating external air positioned intermediate said manifold and said reservoirs.

81. A multifunction dental syringe according to claim 72, wherein said water distribution means comprises a water channel defined by said shank having an upstream end in fluid communication with water tubing disposed within said body and a downstream end defining a water outlet in said nozzle.

82. A multifunction dental syringe according to claim 72, wherein said advancement means comprises
   a first and second chamber disposed within said body and associated with said dental delivery means and said air distribution means;
   a third chamber disposed within said body and associated with said air distribution means; and
   a fourth chamber disposed within said body and associated with said water distribution means.

83. A multifunction dental syringe according to claim 82, wherein said advancement means further comprises
   a piston associated with each of said first and second chambers for reciprocating into at least a portion of said first and second chamber and said reservoirs;
   a plunger associated with each of said first and second chambers attached to one end of said piston and positioned in sealing engagement with said interior walls of said reservoirs;
   an actuator associated with each of said first and second chambers attached to an opposite end of said piston; and
   wherein dental material is advanced from said reservoirs into said dental material passageways and out said at least two dental material outlets in said nozzle when said actuator is depressed and said pressure actuated diaphragm expands into said reservoir under pressure provided by said air distribution means.

84. A multifunction dental syringe according to claim 82, wherein said advancement means further comprises
   a piston associated with each of said third and fourth chambers for reciprocating into at least a portion of said third and fourth chambers;
   a plunger associated with each of said third and fourth chambers and mounted in sealing engagement with interior walls of said third and fourth chambers;
   an actuator associated with each of said third and fourth chambers and attached to an opposite end of said piston; and
   wherein external air and water is advanced through said air and water tubing and out said air and water outlets when said actuator is depressed.

85. A multifunction dental syringe according to claim 72, wherein said light transmitting means comprises a plurality of fiber optic filaments having one end adjacent said external light source and an opposite end adjacent said nozzle.

86. A multifunction dental syringe according to claim 72, further comprising a light source activating means positioned on said grip portion of said syringe for activating and deactivating said external light source.

87. A multifunction syringe according to claim 86, wherein said light source activating means comprises a lever electrically connected to said light source by electrical conduits disposed within said syringe.

88. A multifunction syringe according to claim 86, wherein said light source activating means further comprises a button electrically connected to said light source by electrical conduits disposed within said syringe.

89. A multifunction dental syringe according to claim 72, further comprising a coupling means associated with said grip portion for detachably connecting said syringe to supply hoses of an external instrument delivery system.

90. A multifunction dental syringe according to claim 89, wherein said coupling means comprises a mount integral with said grip portion for receiving a connector, said connector having conduits for conveying air, water, and power from an external instrument delivery system such that said air and water conduits are in fluid communication with said air and water tubing in said body and said power conduit is electrically connected to said electrical conduits disposed within said body.

91. A multifunction dental syringe according to claim 72, wherein said body portion defines a plurality of fill holes adjacent said plurality of reservoirs for providing access to said reservoirs, said fill holes adapted to engage a sealing means for retaining dental material in said reservoirs.

92. A multifunction dental syringe according to claim 91, wherein said sealing means includes a cap screw.

93. A multifunction dental syringe according to claim 91, wherein said sealing means further comprises a stopper of sufficient strength to retain dental material in said reservoirs.

* * * * *